Figure 1:
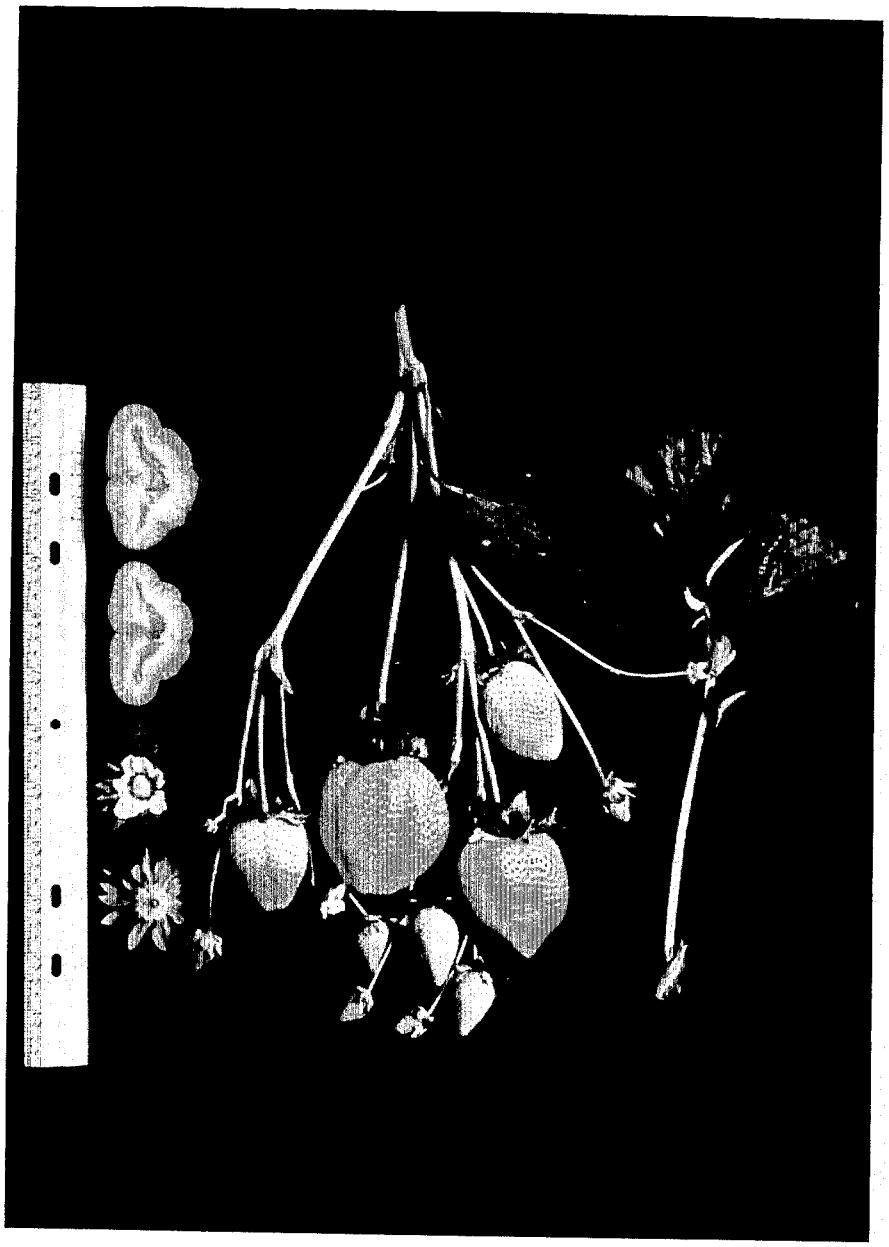

United States Patent [19]

Johnson, Jr.

[11] Patent Number: Plant 5,301

[45] Date of Patent: Oct. 23, 1984

[54] STRAWBERRY PLANT—'THE CROWN'

[75] Inventor: Harold A. Johnson, Jr., Watsonville, Calif.

[73] Assignee: Driscoll Strawberry Associates, Inc., Watsonville, Calif.

[21] Appl. No.: 471,407

[22] Filed: Mar. 2, 1983

[51] Int. Cl.[3] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A new distinct winter planted spring bearing variety of strawberry plant, characterized by its large fruit produced both during the crown crop and subsequent crops. The primary berries have distinct longitudinal furrows. The fruit is produced on long thick pedicels. The hair on pedicels is perpendicular to the pedicel. The berries are considered firm giving the fruit a long shelf life for strawberries. The plant is considered low growing and open, allowing good exposure to its fruit. The leaflets are large, dark rugose. The inflorescences are mostly long which also helps expose its fruit.

1 Drawing Figure

1

This invention relates to a new and distinct variety of strawberry known the "The Crown" and is a result of the cross of the unpatented variety known as the Driscoll Strawberry Associates, Inc. selection B6.117 and the unpatented variety of the Driscoll Strawberry Associates, Inc. selection D5.23.

The seedlings resulting from the aforementioned cross were grown and asexually multiplied in Shasta County, Calif., and tested in the fruiting beds on property of growers of the Driscoll Strawberry Associates, Inc. Clones of the seedlings were also held at the Propagation Nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

In the drawings:

FIG. 1 of the accompanying drawing illustrates plant parts of the new variety, typical in size, shape and color. A berry in cross section illustrates flesh color and characteristic core cavity of primary berries. The inflorescence pictured illustrates typical branching during the middle of July in Watsonville, Calif. The picture shows the long thick pedicels and secondary peduncles. There are six green tertiary berries shown in this picture, all of which will become medium to large berries and are held on pedicels that are long and thick for tertiary pedicels. Many inflorescences may have only primary and secondary berries that develop. This picture also shows a very short common peduncle which is typical. Also shown in the picture is a leaf showing dark, rugose thick leaflets that are cupped upward. Bracts that have developed on the petiole are pictured even though bracts are present on only a fraction of the petioles. A flower is also illustrated with anthers that have dehisced early which is typical. The flower also shows a large, dark calyx, and many large, serrated, overlapping sepals.

The novel plant is medium to large in size, usually less erect and more open than the Driscoll Strawberry Associates, Inc. variety Heidi, U.S. Plant Pat. No. 3,123, even though leaves and individual petioles and leaflets may be equal to, or larger than, Heidi. The Crown

2 variety is adapted as a winter planted variety mainly to central coastal California, and becomes noticeable, even early in April by the prolific crown crop with its large fruit size, much larger in size than that of the Heidi crown crop. If this new variety is given the correct chilling before being planted and doesn't receive too much chilling after being planted, large production continues till late fall. These large berries that are produced continuously on long thick pedicels make this a unique variety. The firmness of the berry, especially its skin, gives the variety a long shelf life. The characteristic longitudinal furrows that are present on the primary berry in the illustration also are distinct. During the main crop in late May and June, pollen may have difficulty reaching the stigmas which are held at a considerable distance from anthers on primary flowers, and cause poorly shaped berries on a percentage of the fruit that develops. These are characteristics that are generally not present on the Heidi. Heidi produces more inflorescence per plant, as well as more total flowers and berries, but the size is greater on the new variety making the total yield usually equal. The Heidi plants and leaves are lighter in color, are not as thick, and have marginal serrations that are deeper and more acute. The berries of the Heidi, along with being a different shape and darker in color, have a skin that isn't as firm as The Crown variety. Heidi has a dessert quality that is sweeter to the taste, but not as conspicuous an aroma as the new variety. The inflorescence of the new variety differs from Heidi in that its common peduncle is shorter, but individual pedicels are longer and thicker. The hair on pedicels of Heidi 20 mm. from tertiary berries lies parallel to the pedicel, while that of The Crown variety is perpendicular to the pedicel. The calyx of the Heidi is large, but that of The Crown variety is even larger and generally darker in color.

The fruit surface of the new invention will crack if subjected to heavy rain, but isn't as prone to Botrytis fruit rot as Heidi during wet weather. The two varieties appear to be equally susceptible to two-spotted spider mite and thrip injury, Mycosphorella leaf spot, but the new variety is more tolerant to powdery mildew. The new variety hasn't been tested against Verticillium wilt, but has withstood the natural invasions of virus in the areas where it has been tested.

The varietal characteristics of the novel plant, decribed below in detail, were observed mainly during July, August and September in the Watsonville area of California, which is a cool coastal area near the ocean. The color terminology is in accordance with the Munsell Color System.

PLANT

Medium in size, considered a low growing open type, but vigorous. The crowns are considered large as they come from the nursery. The plant has an extensive root system.

LEAVES

Medium to large in size. The central leaflet is usually 6 to 9 cm. in length and width, with the length slightly greater than the width. Serrations at margins are medium in depth and have a short-acute apex. Leaflets are considered rugose and thick. Bracts may be present on petioles, but bractless petioles are more common. The color of upper side of leaflet is 8.2GY — 3.2/6.1.

RUNNERS

Runners are vigorous, but medium in abundance both at the nursery and fruiting bed.

INFLORESCENCE

Considered large, average length 30 cm. or more. The main common peduncle is mostly short, averaging less than 10 cm. in length. Secondary peduncles vary in number, but mostly long and thick. Pedicels are also long and thick. Tertiary berries may be absent, but if present are considered large for tertiary berries and are produced on long pedicels. Pedicels holding tertiary fruit may be longer than pedicels holding primary berries with the tertiary berries maturing farther from the common peduncle than the primary berry. Hair on pedicels 20 mm. from the tertiary fruit is held perpendicular to the pedicel. Pedicels holding primary berries usually originate at the axil formed by the union of secondary peduncles, but they may originate from one of the peduncles. Flowers are large and may be visible above the plant. Anthers appear to produce an abundance of pollen during periods of the year, but a limited amount at other times.

FRUIT

Crown crop berriess are considered large, abundant, and showy with subsequent crops also producing berries that are large. Primaries during July average 50 to 55 mm. in length and width. The shape is irregular, primaries are mostly medium to long wedge in outline with longitudinal furrows normal, while secondary and tertiary berries are smoother on the surface and mostly medium to long conic to medium wedge in outline as described in the USDA Bulletin 1043. The shoulders at the calyx end are rounded, not necked. It is not uncommon for primary berries to have seed at the apex unfertilized producing misshaped berries that may even split open exposing the fruit core. The fruit skin and flesh is considered firm. The seed is medium in size and is held equal to or exerted above the fruit surface. The color of the seed is yellow, but darkens easily when exposed to the sun. The dessert quality is rated by panels as medium to good, but not high in sweetness. The color of the fruit surface is 8.4R — 2.9/9.4 and the flesh is 8.3R — 3.5/13.0.

CALYX

Larger in diameter on primary berries, average 50 mm. or more in diameter. Sepals are abundant, with considerable overlap and serrations present. Serrations may be noticeably deep, but shallow or lacking on sepals of tertiary or secondary berries, (see illustration). The calxy may be flexed on large berries that have round shoulders with the calyx attached to the berry below the outline of the berry, when viewing the fruit from the side, but most calyx are held next to the surface. The color of sepals on the side facing the fruit is 7.4 GY — 2.3/4.0.

I claim:

1. The new and distinct strawberry plant herein described and illustrated, and identified by the characteristics enumerated above.

* * * * *